(12) United States Patent
Marcolino Quintao Severgnini et al.

(10) Patent No.: US 11,944,420 B2
(45) Date of Patent: Apr. 2, 2024

(54) ELECTRODERMAL ACTIVITY ACQUISITION

(71) Applicant: Toyota Motor Engineering & Manufacturing North America, Inc., Plano, TX (US)

(72) Inventors: Frederico Marcolino Quintao Severgnini, Ann Arbor, MI (US); Ercan Mehmet Dede, Ann Arbor, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 624 days.

(21) Appl. No.: 17/003,338

(22) Filed: Aug. 26, 2020

(65) Prior Publication Data

US 2022/0061692 A1 Mar. 3, 2022

(51) Int. Cl.
*A61B 5/0531* (2021.01)
*A61B 5/16* (2006.01)

(52) U.S. Cl.
CPC ............ *A61B 5/0531* (2013.01); *A61B 5/165* (2013.01); *A61B 2562/0209* (2013.01)

(58) Field of Classification Search
CPC ..... A61B 5/0531; A61B 5/0533; A61B 5/053; A61B 5/6843; A61B 5/165; A61B 2562/0209; A61B 2562/0215; A61B 2560/0468
See application file for complete search history.

(56) References Cited

U.S. PATENT DOCUMENTS 5,789,659 A * 8/1998 Williams ............. G01N 33/007
73/31.06
9,135,803 B1 9/2015 Fields et al.
(Continued)

FOREIGN PATENT DOCUMENTS

DE 102013021823 A1 * 6/2015 ........... A61B 5/0533
DE 102014211406 A1 8/2015

OTHER PUBLICATIONS

DE-102013021823-A1 Machine Translation (Year: 2015).*
(Continued)

*Primary Examiner* — Alex M Valvis
*Assistant Examiner* — Nidhi N Patel
(74) *Attorney, Agent, or Firm* — Christopher G. Darrow; Darrow Mustafa PC (57) ABSTRACT

The measurement of electrodermal activity (EDA) can be facilitated by a sensing surface. The sensing surface can have a plurality of electrode pairs. An electrode pair can include a first electrode and a second electrode that are electrically isolated from each other. The plurality of electrode pairs can be electrically isolated from each other. A distance between neighboring electrode pairs can be larger than a distance between the first electrode and a second electrode of each electrode pair. One or more sensors can be configured to detect contact with the sensing surface. In response to the one or more sensors detecting contact with the sensing surface, one or more electrode pairs can be selected to be activated. In response to the one or more electrode pairs being selected to be activated, the selected one or more electrode pairs can be activated.

20 Claims, 4 Drawing Sheets

(56) References Cited

U.S. PATENT DOCUMENTS

| | | | | |
|---|---|---|---|---|
| 2013/0317318 A1* | 11/2013 | Tartz | ............... | A61B 5/7221 |
| | | | | 600/301 |
| 2015/0258995 A1* | 9/2015 | Essers | ............... | G08G 1/163 |
| | | | | 340/576 |
| 2020/0338334 A1* | 10/2020 | Toong | ............ | A61N 1/0476 |

OTHER PUBLICATIONS

Zangroniz, R. et al., "Electrodermal Activity Sensor for Classification of Calm/Distress Condition," Sensors 2017, 17 (14 pages).

Araki, S. et al., "Exploring Multi-Channel Features for Denoising-Autoencoder-Based Speech Enhancement," 2015 IEEE International Conference on Acoustics, Speech and Signal Processing (ICASSP) pp. 116-120 (5 pages).

Biopac Systems, Inc., "MP36R 4-Channel Systems", retrieved from the Internet: <http://www.biopac.com/product-category/research/systems/mp36r-4-channel-systems/>, retrieved Aug. 26, 2020 (4 pages).

Shimmer, "Shimmer3 GSR+ Unit", retrieved from the Internet: <http://www.shimmersensing.com/shimmer-website-membership/>, retrieved Aug. 26, 2020 (5 pages).

Empatica Inc., "Embrace2", retrieved from the Internet: <http://www.empatica.com/embrace2/>, retrieved Aug. 26, 2020 (10 pages).

* cited by examiner

Detecting contact with a sensing surface
310

Selecting the one or more electrode pairs to activate
320

Causing the selected one or more electrode pairs to be activated
330

FIG. 4B

ELECTRODERMAL ACTIVITY ACQUISITION

FIELD

The subject matter described herein relates in general to electrodermal activity (EDA) and, more particularly, to acquiring EDA.

BACKGROUND

Electrodermal activity (EDA) is a biosensing technique used in psychology and medicine to detect emotional arousal, measure distress levels, and/or predict seizures, among other things. EDA is the measurement of skin transpiration in the palm and/or fingers of a user. An emotional state of the user can be identified based on the determined EDA.

SUMMARY

In one respect, the subject matter presented herein relates to a method for measuring electrodermal activity (EDA). The method can include detecting, using one or more sensors, contact with a sensing surface. The sensing surface can have a plurality of electrode pairs. Each electrode pair can include a first electrode and a second electrode. The first electrode and the second electrode can be electrically isolated from each other. The plurality of electrode pairs can be electrically isolated from each other. A distance between neighboring electrode pairs can be larger than a distance between the first electrode and a second electrode of each electrode pair. The method can include, in response to detecting the contact with the sensing surface, selecting one or more electrode pairs to activate. The method can include, in response to selecting one or more electrode pairs to activate, causing the selected one or more electrode pairs to be activated.

In another respect, the subject matter presented herein relates to a system for measuring electrodermal activity. The system can include a sensing surface. The sensing surface can have a plurality of electrode pairs. Each electrode pair can include a first electrode and a second electrode. The first electrode and the second electrode can be electrically isolated from each other. The plurality of electrode pairs can be electrically isolated from each other. A distance between neighboring electrode pairs can be larger than a distance between the first electrode and a second electrode of each electrode pair. The system can include one or more sensors. The one or more sensors can be configured to detect contact with the sensing surface. The system can include one or more processors. The one or more processors can be operatively connected to the plurality of electrode pairs. The one or more processors can be operatively connected to the one or more sensors. The one or more processors can be programmed to initiate executable operations that include, responsive to detecting contact with the sensing surface, selecting one or more electrode pairs to activate, and, responsive to selecting one or more electrode pairs to activate, causing the selected one or more electrode pairs to be activated.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

DETAILED DESCRIPTION

Electrodermal Activity (EDA) can be used to determine a user's emotional state. Electronic devices and vehicles that can access the EDA of the user can adapt their functions to accommodate the user's emotional state. However, in order to accurately capture EDA and reduce the occurrence of noise in the measured EDA, electrodes are glued (or otherwise attached) to and/or hardly pressed against the user's skin. Electrodes that are neither glued nor hardly pressed against the skin may result in friction as the user moves, which, in turn, can generate significant noise in the measurements. As such, the user may experience discomfort with the electrodes being glued to the user's skin, and may find the technique invasive.

Arrangements presented herein are directed to acquisition systems and methods for capturing EDA. The EDA acquisition system can include a sensing surface, which can be rigid or compliant. EDA data can be captured when the user touches the sensing surface. More particularly, EDA data can be captured when a portion of the user's hand (e.g., fingers or palm) or other portion of the body is in contact with the sensing surface.

As an example, the sensing surface can include a plurality of electrodes. The electrodes can capture EDA without being glued or pressed into the skin of the user. In some arrangements, the EDA acquisition system can apply a noise-cancelling algorithm to the captured EDA to achieve a high signal-to-noise ratio. The sensing surface can be incorporated into one or more vehicle structures, such as a steering wheel, a touchscreen, and/or a touchpad. The electrodes of the sensing surface can be exposed on the surface, or they can be located under the surface of the vehicle structure. The resulting EDA measurement can be transmitted to any interested entity (e.g., a vehicle system, a mobile device, and/or a server).

Detailed embodiments are disclosed herein; however, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-4, but the embodiments are not limited to the illustrated structure or application.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details.

Figure 1:
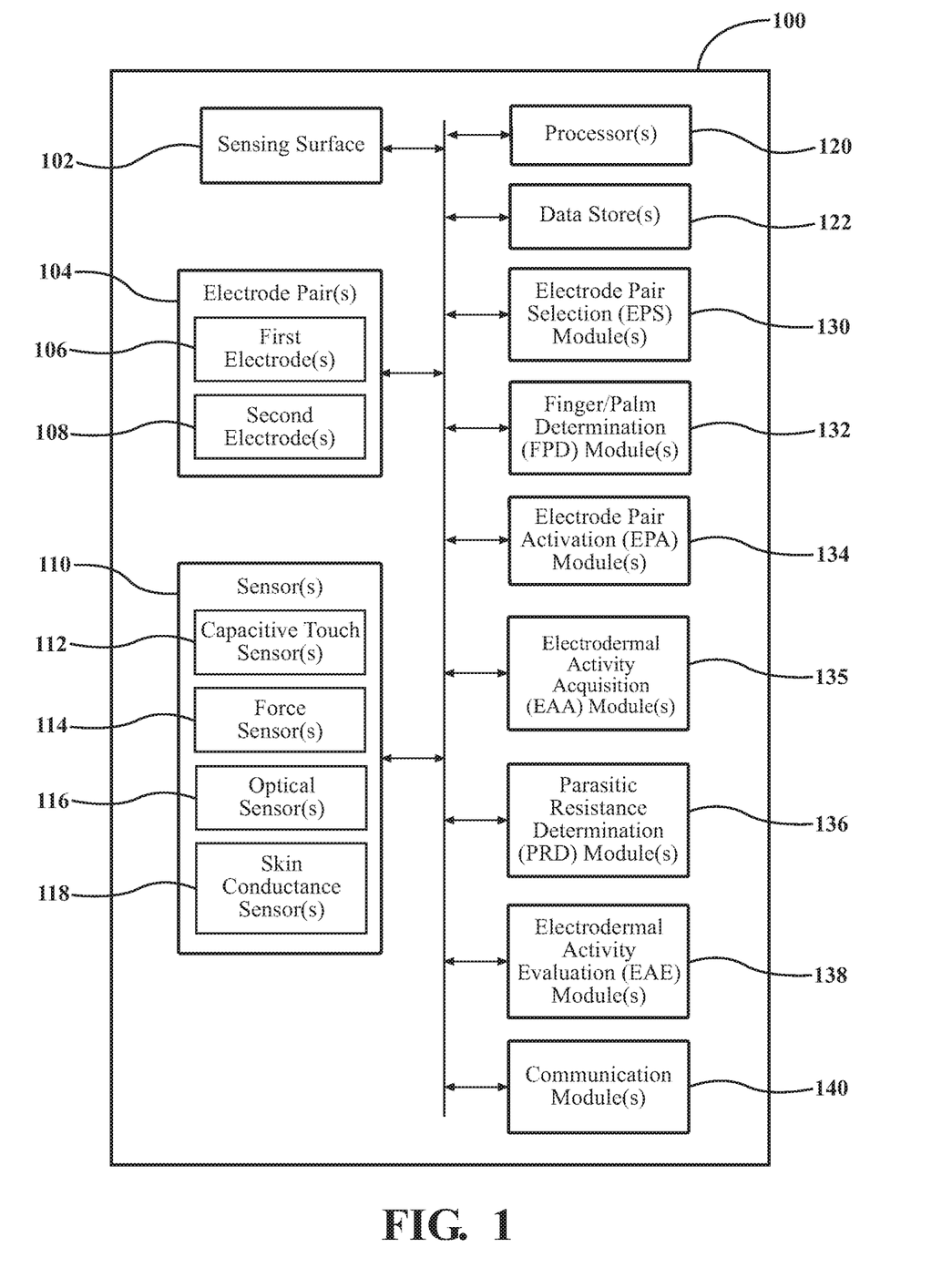
FIG. 1 is an example of an electrodermal activity (EDA) acquisition system.

Referring to FIG. 1, an example of electrodermal activity (EDA) acquisition system 100 is shown. The EDA acquisition system 100 can include various elements, which can be communicatively linked in any suitable form. As an example, the elements can be connected as shown in FIG. 1. Some of the possible elements of the EDA acquisition system 100 are shown in FIG. 1 and will now be described. It will be understood that it is not necessary for the EDA acquisition system 100 to have all of the elements shown in FIG. 1 or described herein. The EDA acquisition system 100 can have any combination of the various elements shown in FIG. 1. Further, the EDA acquisition system 100 can have additional elements to those shown in FIG. 1. In some arrangements, the EDA acquisition system 100 may not include one or more of the elements shown in FIG. 1. Further, it will be understood that one or more of these elements can be physically separated by large distances.

The EDA acquisition system can include one or more sensing surfaces 102. The sensing surface 102 can include a plurality of electrode pairs 104, and one or more skin conductance sensors 118. The sensing surface 102 can include an electrically insulating material. The sensing surface 102 can include a rigid surface, which is a surface that can maintain its shape when a pressure is exerted on it (e.g., polymer). Alternatively, the sensing surface 102 can be a compliant surface, which is a surface that deviate from its original shape in response to a pressure being exerted on it (e.g., Polydimethylsiloxane (PDMS) or rubber). The sensing surface 102 can be of any material that does not conduct electricity and can be suitable for at least partially embedding the electrode pairs 104. The one or more sensing surfaces 102 can be integrated into any suitable vehicle component, such as human interface devices, steering wheels, touchpads, track pads, and/or touch screens.

The sensing surface(s) 102 can be formed using any suitable method, e.g., conventional printed circuit board (PCB) manufacturing technology, flex circuit manufacturing technology where thin electrodes are embedded in a flexible KAPTON® substrate, screen printing or multi-material additive manufacturing.

Each electrode pair 104 can include a first electrode 106 and a second electrode 108. The first and second electrodes 106, 108 can be at least partially embedded in the sensing surface 102. In some arrangements, a portion of the first electrode 106 and a portion of the second electrode 108 can be embedded in the sensing surface 102 and a portion of the first electrode 106 and a portion of the second electrode 108 can be exposed on the sensing surface 102. In some arrangements, the exposed portions of the first and second electrodes 106, 108 can be substantially flush with the rest of the sensing surface 102. In some arrangements, the first electrode 106 and the second electrode 108 can be embedded in the sensing surface 102 such that the first electrode 106 and the second electrode 108 are not exposed to the sensing surface 102. In such case, the first electrode 106 and the second electrode 108 can be located just under the outer surface of the sensing surface 102. The first electrode 106 and the second electrode 108 can be electrically isolated from each other within the sensing surface 102. When the first electrode 106 and the second electrode 108 are activated, there can be substantially low electric current travelling through the sensing surface 102 between the first electrode 106 and the second electrode 108. The current can be at a biocompatible level that is undetectable when the sensing surface 102 is touched by a portion of a human's body.

The first and second electrodes 106, 108 can be of any material suitable for permitting skin conductance and acquiring electrodermal activity. As an example, the first and second electrodes 106, 108 can be standard silver-silver chloride (Ag/AgCl) electrodes. As another example, the first and second electrodes 106, 108 can be stainless steel electrodes.

Figure 2:
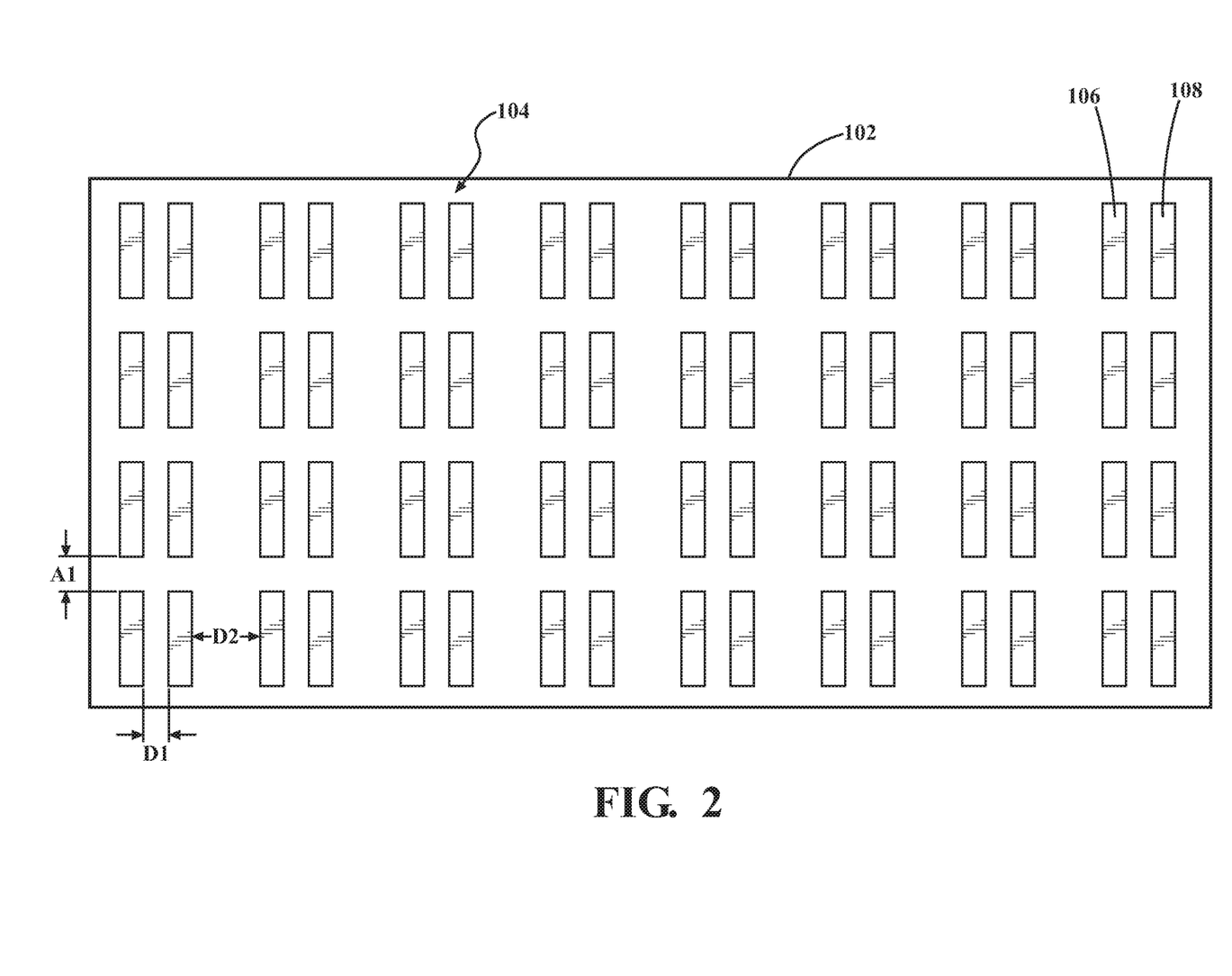
FIG. 2 is an example of a sensing surface.

The electrode pairs 104 can be arranged in any suitable manner. As an example, the electrode pairs 104 can be arranged in a grid-like pattern as shown in FIG. 2. In some arrangements, the electrode pairs 104 can be arranged in an interdigitated or non-interdigitated matrix configuration. The sensing surface 102 can be mapped such that the exact location of each electrode and each electrode pair is known. For instance, the sensing surface 102 can be mapped using Cartesian coordinates (x, y) or other coordinates such that each electrode 106, 108 and/or electrode pair 104 can be identified by their coordinates of the sensing surface 102 proximate to the electrode's and/or electrode pair's location respectively.

The electrode pairs 104 can be electrically isolated from each other. In such a case, there is substantially no electric current travelling through the sensing surface 102 from one electrode pair 104 to another electrode pair 104. In one or more arrangements, the first electrode 106 can be a negative electrode, and the second electrode 108 can be the positive electrode. In such cases, the negative electrode of the electrode pairs 104 can be electrically connected to each other and the positive electrode of the electrode pairs 104 can be electrically connected. Thus, the negative electrode from the electrode pairs 104 can share an electric potential value and can behave like a single negative electrode. The positive electrode from the electrode pairs 104 can share an electric potential value and can behave like a single positive electrode. As an alternative, the negative electrodes of the electrode pairs 104 may not be electrically connected and/or the positive electrodes of the electrode pairs 104 may not be electrically connected. The electrode pairs 104 can be activated and/or deactivated using any suitable means such as one or more control switches. The electrode pairs 104 can be activated and/or deactivated individually or as a group. As an example of such a case, a single control switch can activate or deactivate a single electrode pair 104 or a group of two or more electrode pairs 104.

In one or more arrangements, distance between the first electrode 106 and the second electrode 108 of the plurality of electrode pairs 104 can be substantially equal. The first electrode 106 and the second electrode 108 of the electrode pairs 104 can be substantially equidistant. The distance between two neighboring electrode pairs 104 can be larger than the distance between the first electrode 106 and a second electrode 108 of the electrode pairs 104. The larger the difference between the distance between neighboring electrode pairs 104 and the distance between the first and the second electrodes 106, 108, the more negligible the parasitic voltage drop and/or parasitic resistance between the neighboring electrode pairs 104. Parasitic resistance between activated electrode pairs 104 can cause a parasitic voltage drop between the electrode pairs 104, which can lead to false or inaccurate EDA measurements.

The EDA acquisition system 100 can include one or more processors 120. "Processor" means any component or group of components that are configured to execute any of the processes described herein or any form of instructions to carry out such processes or cause such processes to be performed. The processor(s) 120 can be implemented with one or more general-purpose and/or one or more special-purpose processors. Examples of suitable processors include microprocessors, microcontrollers, DSP processors, and other circuitry that can execute software. Further examples of suitable processors include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller. The processor(s) 120 can include at least one hardware circuit (e.g., an integrated circuit) configured to carry out instructions contained in program code. In arrangements in which there is a plurality of processors 120, such processor(s) 120 can work independently from each other or one or more processor(s) 120 can work in combination with each other. In one or more arrangements, one or more processor(s) 120 can be a main processor(s) of a vehicle. For instance, one or more processor(s) 120 can be electronic control unit(s) (ECU).

The EDA acquisition system 100 can include one or more data stores 122 for storing one or more types of data. The data store(s) 122 can include volatile and/or non-volatile memory. Examples of suitable data store(s) 122 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store(s) 122 can be a component of the processor(s) 120, or the data store(s) 122 can be operatively connected to the processor(s) 120 for use thereby. The term "operatively connected," as used throughout this description, can include direct or indirect connections, including connections without direct physical contact.

In one or more arrangements, the data store(s) 122 can include historical data for the electrode pairs 104. The historical data can be provided in any suitable form. As an example, the historical data can be in a tabulated format with each electrode pair 104 identified using any suitable identifier such as a unique number. Non-limiting examples of the historical data can include previously measured signal strengths or quality of the electrode pair 104, value of parasitic resistance between the electrode pair 104 and its neighboring electrode pairs 104, the number of times the electrode pair 104 has been used within a certain time period, and/or a percentage value indicating the frequency of use of the electrode pair 104 in relation to an overall use of the EDA acquisition system 100.

Parasitic resistance can occur between two or more electrode pairs 104 that are activated. The value of the parasitic resistance can be determined based on the distance and material between the two activated electrode pairs 104. Additionally and/or alternatively, the value of the parasitic resistance can be determined at the time of manufacture and can be stored in the historical data for the electrode pairs 104. In one or more arrangements, the data store(s) 122 can include user data, such as a fingerprint and/or a handprint of one or more users. In some instances, the user data can include information about the size and/or shape of the hand of one or more users. User data can include information relating to hand, finger and/or palm placement in relation to the sensing surface. Such user data can be based on average human data, user specific data, learned user data, and/or any combination thereof.

The EDA acquisition system 100 can include one or more sensors 110. "Sensor" means any device, component and/or system that can detect, determine, assess, monitor, measure, quantify, acquire, and/or sense something. The sensor(s) can detect, determine, assess, monitor, measure, quantify, acquire, and/or sense in real-time. As used herein, the term "real-time" means a level of processing responsiveness that a user or system senses as sufficiently immediate for a particular process or determination to be made, or that enables a processor to keep up with some external process. Data acquired by the one or more sensors can be stored in the data store(s).

In arrangements in which there is a plurality of sensors 110, the sensors 110 can work independently from each other. Alternatively, two or more of the sensors 110 can work in combination with each other. In such case, the two or more sensors 110 can form a sensor network. The sensors 110 can be attached to or embedded into the sensing surface 102. The one or more sensors 110 can be operatively connected to the processor(s) 120, the data store(s) 122, and/or other element of the EDA acquisition system 100 (including any of the elements shown in FIG. 1).

The sensor(s) 110 can be any suitable type of sensor. Various examples of different types of sensors will be described herein. However, it will be understood that the embodiments are not limited to the particular sensors described.

The sensors 110 can include one or more capacitive touch sensors 112. The capacitive touch sensor(s) 112 can detect and measure anything that is conductive or has a dielectric different from air based on capacitive coupling. The capacitive touch sensor(s) 112 can detect and measure proximity, pressure, position and displacement, force, humidity, and/or acceleration. The capacitive touch sensor(s) 112 can be used in connection with the sensing surface 102. In one or more arrangements and as an example, the capacitive touch sensor(s) 112 can be embedded into the sensing surface 102 and the capacitive touch sensor(s) 112 can detect contact with the sensing surface 102. The capacitive touch sensor(s) 112 can detect how much surface area of the sensing surface 102 is in contact with an object (e.g., a hand or a finger).

The sensors 110 can include one or more force touch sensors 114. In one or more arrangements and as an example, the force touch sensor(s) 114 can distinguish between various levels of force applied to the sensing surface 102. The force touch sensor(s) 114 can measure the pressure and/or the weight of a finger and/or a hand and determine that there is contact with an object.

The sensors 110 can include one or more optical sensors 116. The optical sensor(s) 116 can detect contact based on the presence and/or absence of light. As an example, the optical sensor(s) 116 can include infrared emitters that emit infrared light and infrared image sensors that detect infrared light. The infrared image sensors can detect when an object touches the sensing surface 102 and blocks a portion of the infrared light from being received by the infrared image sensors. In one or more arrangements and as another example, the optical sensor(s) 116 can detect contact with the sensing surface 102 based on an object touching the surface and the optical sensor(s) 116 detecting an absence of light. The location of the contact and the size of the contact area can be calculated by using information from the optical sensor(s) 116 and mathematical triangulation. In one or more arrangements, the optical sensors 116 can include one or more cameras.

The sensors 110 can include one or more skin conductance sensor(s) 118. The skin conductance sensor(s) 118 can acquire EDA by measuring the conductivity of skin and/or sweat on the user's fingers and/or palm. In one or more arrangements, the skin conductance sensor(s) 118 can apply a constant voltage (e.g., 0.5V) to the first and second electrodes 106, 108 that are in contact with the skin, creating a circuit. The skin conductance sensor(s) 118 can calculate the conductivity of the skin and/or sweat by measuring the current flowing through the first and second electrodes 106, 108. As an example, each electrode pair 104 can include a skin conductance sensor(s) 118 for measuring the skin conductance at that respective electrode pair 104. Skin conductance can be expressed in micro-siemens. As an example, the skin conductance sensor(s) 118 can be designed to measure minute ($1/1000$) micro-siemens relative changes in sweat activity.

The EDA acquisition system 100 can include one or more modules, which will be described herein. The modules can be implemented as computer readable program code that, when executed by a processor, implement one or more of the various processes described herein. One or more of the modules can be a component of the processor(s) 120, or one or more of the modules can be executed on and/or distributed among other processing systems to which the processor(s) 120 is operatively connected. The modules can include instructions (e.g., program logic) executable by one or more processor(s) 120. Alternatively or in addition, one or more data store 122 may contain such instructions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

The EDA acquisition system 100 can include one or more electrode pair selection (EPS) modules 130. The EPS module(s) 130 can be configured to select one or more electrode pairs 104 to activate in response to contact with the sensing surface 102 being detected. The EPS module 130 can receive information from the sensors 110 indicating which portions (if any) of sensing surface 102 are in contact with an object. The information can include, as an example, Cartesian coordinates of the portions in contact with an object. The EPS module 130 can identify the electrode pair(s) 104 proximate to the Cartesian coordinates. Upon identifying the electrode pair(s) 104 proximate to the Cartesian coordinates, the EPS module 130 can select one or more electrode pairs 104 to activate. In some arrangements, the selection of the electrode pair(s) 104 to activate can be based on additional or alternative factors, including at least one of signal quality and historical data. The EPS module 130 can select the electrode pairs 104 to activate based on any other suitable criteria such as to maximize the distance between the selected electrode pairs 104, which can reduce parasitic voltage drop.

To select the electrode pairs 104 to activate based on signal strength, the EPS module 130 can measure the skin conductance level for the electrode pairs 104 that are in contact with an object and select the electrode pairs 104 with a strong signal. To determine the electrode pairs 104 with strong signals, the EPS module 130 can determine a threshold value that the measured skin conductance can meet or exceed.

In some arrangements, the EPS module 130 can activate the electrode pairs 104 that have been identified as being in contact with an object. To activate an electrode pair 104, electrical energy can be supplied to the electrode pair 104. The first and second electrodes 106, 108 can be made active with opposite polarities. As an example, the first electrode 106 can have a negative polarity, and the second electrode 108 can have a positive polarity. Alternatively, the first electrode 106 can have a positive polarity, and the second electrode 108 can have a negative polarity. The EPS module 130 can measure the skin conductance through the activated electrode pairs 104. If the measured skin conductance level meets or exceeds the threshold value, the EPS module 130 can determine that the electrode pair 104 has a strong signal and select the electrode pair 104 to be activated for measuring electrodermal activity. If the measured skin conductance level does not meet the threshold value, the EPS module 130 can determine that the electrode pair 104 does not have a strong signal and can determine not to select the electrode pair 104 for measuring electrodermal activity. The EPS module 130 can update signal strength of the electrode pair 104 in the historical data.

To select the electrode pairs 104 to activate based on historical data, the EPS module 130 can, as an example, determine the frequency with which the electrode pairs 104 in contact with an object are selected for measuring electrodermal activity. As another example, the EPS module 130 can determine the previously measured signal strength of the electrode pairs. In some arrangements, the EPS module 130 can select the electrode pairs 104 that are most frequently used to measure electrodermal activity. In some other arrangements, the EPS module 130 can select the electrode pairs 104 that are least frequently used to measure the electrodermal activity. In some other arrangements, the EPS module 130 can select the electrode pairs 104 that were used in a preceding session of measuring the electrodermal activity.

As an example, the EPS module 130 can receive the historical data from the data store 122. The EPS module 130 can determine, based on the received historical data, the frequency of use of the electrode pairs 104 in contact with an object and/or the previously measured signal strength of the electrode pair 104. The EPS module 130 can sort the electrode pairs 104 in contact from most frequently used to least frequently used, and/or from the electrode pair 104 with the highest previously measured signal strength to the electrode pair 104 with the lowest previously measured signal strength. The EPS module 130 can use any suitable algorithm to select the electrode pairs 104 to be activated. As an example, the EPS module 130 can select a certain number (e.g., one, more than one, or all) of electrode pairs 104 that meet a criteria, e.g., a frequency of use level or a signal strength level, to be activated for measuring electrodermal activity.

The EDA acquisition system 100 can include one or more finger/palm determination (FPD) module(s) 132. The FPD module(s) 132 can be configured to determine whether a user's finger and/or palm is in contact with the sensing surface 102. The FPD module(s) 132 can determine the area of contact with the sensing surface 102 based on the perimeter of the contact area. The FPD module(s) 132 can determine the size and/or the shape of the contact area based on, as an example, the x-, y-coordinates of the contact area. The FPD module(s) 132 can determine and/or distinguish between a finger and a palm based on size and shape as fingers tend to be narrower and longer than palms which tend to be wider and shorter.

In some arrangements, the FPD module(s) 132 can receive a finger print and/or handprint from a suitable sensor (e.g., fingerprint scanner, hand scanner, camera, etc.). In such arrangements, the FPD module(s) 132 can compare the fingerprint and/or handprint received from the sensor with fingerprint and/or handprint data in the user data stored in the data store(s) 122. If the FPD module(s) 132 detects a match with the fingerprint, the FPD module(s) 132 can determine that the object in contact with the sensing surface 102 is a finger. If the FPD module(s) 132 detects a match with the handprint in the user data, the FPD module(s) 132 can determine that the object in contact with the sensing surface 102 is a palm.

In addition to the above examples, the FPD module(s) 132 can include any suitable object recognition software to detect whether the contact is being made by a user's finger, palm, both, or neither. The FPD module(s) 132 can use any suitable technique, including, for example, template matching and other kinds of computer vision and/or image processing techniques and/or other artificial or computational intelligence algorithms or machine learning methods. In some arrangements, the FPD module(s) 132 can tag the selected electrode pairs 104 that are in contact with the user's palm as being in contact with the user's palm. Additionally and/or alternatively, the FPD module(s) 132 can tag the selected electrode pairs 104 that are in contact with the user's finger(s) as being in contact with the user's finger(s).

The EDA acquisition system 100 can include one or more electrode pair activation (EPA) module(s) 134. The EPA module(s) 134 can be configured to cause the one or more electrode pairs 104 to be activated or remain in an activated condition in response to the one or more electrode pairs 104 being selected. In some arrangements, the EPA module(s) 134 can be configured to deactivate or keep in a deactivated condition one or more non-selected electrode pairs. In some arrangements, the EPA module(s) 134 can be configured to cause the electrode pairs 104 tagged as being in contact with the user's palm and/or the electrode pairs 104 tagged as being in contact with the user's finger(s) to be activated. In cases where each of the electrode pairs 104 is operatively connected to an individualized control switch, the EPA module(s) 134 can power up the control switch(es) for the selected electrode pairs 104. Upon being powered up, the control switch(es) can activate the electrode pair(s) 104. In such cases and as previously mentioned, the first and second electrodes 106, 108 can be set to opposite polarities and a small voltage can be applied between the first and second electrodes 106, 108.

The EDA acquisition system 100 can include one or more electrodermal activity acquisition (EAA) module(s) 135. The EAA module(s) 135 can be configured to acquire EDA data from a user based on the contact with the sensing surface 102, using the activated electrode pairs 104. In one or more arrangements, the EAA module(s) 135 can cause the skin conductance sensor(s) 118 associated with the activated electrode pairs 104 to be activated. The skin conductance sensor(s) 118 can measure the skin conductance across the activated electrode pairs 104, and the EAA module(s) 135 can receive the EDA data and the related electrode pairs 104 associated with the EDA data. Acquiring EDA data from the user can include measuring EDA using at least one of skin potential, resistance, conductance, admittance, and impedance. Skin potential can be the voltage measured between the first and second electrodes 106, 108 of an activated electrode pair 104. Skin resistance can be the resistance measured between the first and second electrodes 106, 108 of the activated electrode pair 104. Skin conductance can be the measurement of the electrical conductivity of the skin between the first and second electrodes 106, 108 of the activated electrode pair 104. Skin admittance is determined by measuring relative permittivity and the resistivity of the skin, and by contact ratio between dry electrodes and skin. Skin impedance can be the measurement of the impedance of the skin to alternating current of low frequency.

The EDA acquisition system 100 can include one or more parasitic resistance determination (PRD) modules 136. The PRD module(s) 136 can be configured to determine the parasitic resistance between two or more activated electrode pairs 104. The PRD module(s) 136 can receive information indicating the electrode pairs 104 selected to be activated. In one or more arrangements, the PRD module(s) 136 can calculate the parasitic resistance between two electrode pairs 104 based on the distance and/or the material between the electrode pairs 104. Alternatively or additionally, the PRD module(s) 136 can access the historical data of the electrode pair 104 and retrieve from the historical data, the parasitic resistance for the electrode pair 104 based on whether any of the neighboring electrode pairs 104 have been selected to be activated. The PRD module(s) 136 can use any suitable method to calculate the parasitic resistance.

The EDA acquisition system 100 can include one or more electrodermal activity evaluation (EAE) module(s) 138. In one or more arrangements, the EAE module(s) 138 can be configured to evaluate the EDA data based on one or more factors. As an example, the EAE module(s) 138 can be configured to evaluate the EDA data based on the determination of whether the user's finger or palm is in contact with the sensing surface 102. The range of EDA data acquired from the fingers can differ significantly from the range of EDA data acquired from the palm such that evaluating the EDA data from the fingers and palm together can lead to inaccuracies. As such the EAE module(s) 138 can evaluate the EDA data for the palms or the EDA data for the fingers. In cases where the EAE module(s) 138 evaluates EDA data for the palms and the fingers, the EAE module(s) 138 can evaluate the EDA for the palm(s) separate from EDA data for the finger(s).

In cases when there are activated electrode pairs 104 in contact with the user's palm or the user's finger(s) but not both, the EAE module(s) 138 can conduct further analyses with the activated electrode pairs 104. In the case where the activated electrode pairs 104 include electrode pairs 104 in contact with the user's palm and electrode pairs 104 in contact with the user's finger(s), the EAE module(s) 138 can group the EDA data into a first group, where the electrode pairs 104 are in contact with a finger and a second group, where the electrode pairs 104 are in contact with a palm. The EAE module(s) 138 can determine which one of the two groups to select for further analysis. Alternatively, the EAE module can continue with the two groups for further analysis.

The EAE module(s) 138 can be configured to evaluate the EDA data based on the determined parasitic resistance. The parasitic resistance can affect the EDA data, leading to inaccuracies. As such, the EAE module(s) 138 can adjust the EDA data so as to take the parasitic resistance into account. As an example, the EAE module(s) 138 can subtract the parasitic resistance from the EDA calculations.

The EAE module(s) 138 can use any suitable calculations and/or algorithms to evaluate and determine accurate EDA data. The EAE module(s) 138 can identify and reduce noise in the EDA data measurement. The EAE module(s) 138 can compare EDA data received from two or more activated electrode pairs 104 to identify noise. The EAE module(s) 138 can apply any suitable machine learning techniques to learn how to receive noisy EDA data from the electrode pairs 104 and reconstruct the noisy EDA data into one or more EDA measurements with low signal-to-noise ratio. The EAE module(s) 138 can evaluate the one or more EDA measurements to determine the emotional state of the user. Alternatively or additionally, the single resulting EDA measurement can be transmitted to any interested entity.

The EDA acquisition system 100 can include one or more communication modules 140. A "communication module" refers to a component designed to transmit and/or receive information from one source to another. The communication module(s) 140 can transmit and/or receive information via one or more communication networks. The communication network(s) can include an internal communication network as well as an external communication network.

The internal communication network can include a bus and/or other wired and/or wireless mechanisms. The elements of the EDA acquisition system 100 such as the data store 122, the sensors 110, and the processor(s) 120 can be communicatively linked to each other through the internal communication network. Each of the elements of the EDA acquisition system 100 can include and/or execute suitable communication software, which enables the various elements to communicate with each other through the communication network and perform the functions disclosed herein.

The external communication network represents one or more mechanisms by which the EDA acquisition system 100 can communicate with other entities, e.g., a mobile device, a vehicle system, and/or a server. For instance, the EDA acquisition system 100 can send EDA data to a mobile device, a vehicle safety system, and/or a server. The external communication network can include any suitable communication mechanism such as a Wi-Fi hotspot.

Referring to FIG. 2, an example of a sensing surface 102 is shown. As an example and as shown in FIG. 2, the sensing surface 102 can include the plurality of electrode pairs 104. The electrode pairs 104 can be arranged in any suitable manner. For example, as shown, the electrode pairs 104 can be arranged in a grid format.

The distance D1 between the first and second electrode 106, 108 of each electrode pair 104 can be substantially equal. The distance A1, D2 between neighboring electrode pairs 104 can be significantly larger (e.g., 2, 3, 4, 5 or more times larger) than the distance D1 between the first and second electrodes 106, 108. In some arrangements, the distance A1, D2 between neighboring electrode pairs 104 can be substantially equal across the sensing surface 102.

With the distance D1 between the first and second electrode 106, 108 of the electrode pairs 104 being substantially equal, the resistance between the first and second electrodes 106, 108 of the electrode pairs 104 can be substantially equal. Having the voltages, resistances, and currents of the electrode pairs 104 be substantially equal to the voltage, resistance, and current of other electrode pairs 104 respectively can reduce the processing power required for evaluating the EDA data.

Now that the various potential systems, devices, elements and/or components of the EDA acquisition system 100 have been described, various methods will now be described. Various possible steps of such methods will now be described. The methods described may be applicable to the arrangements described above in relation to FIGS. 1-2, but it is understood that the methods can be carried out with other suitable systems and arrangements. Moreover, the methods may include other steps that are not shown here, and in fact, the methods are not limited to including every step shown. The blocks that are illustrated here as part of the methods are not limited to the particular chronological order. Indeed, some of the blocks may be performed in a different order than what is shown and/or at least some of the blocks shown can occur simultaneously.

Figure 3:
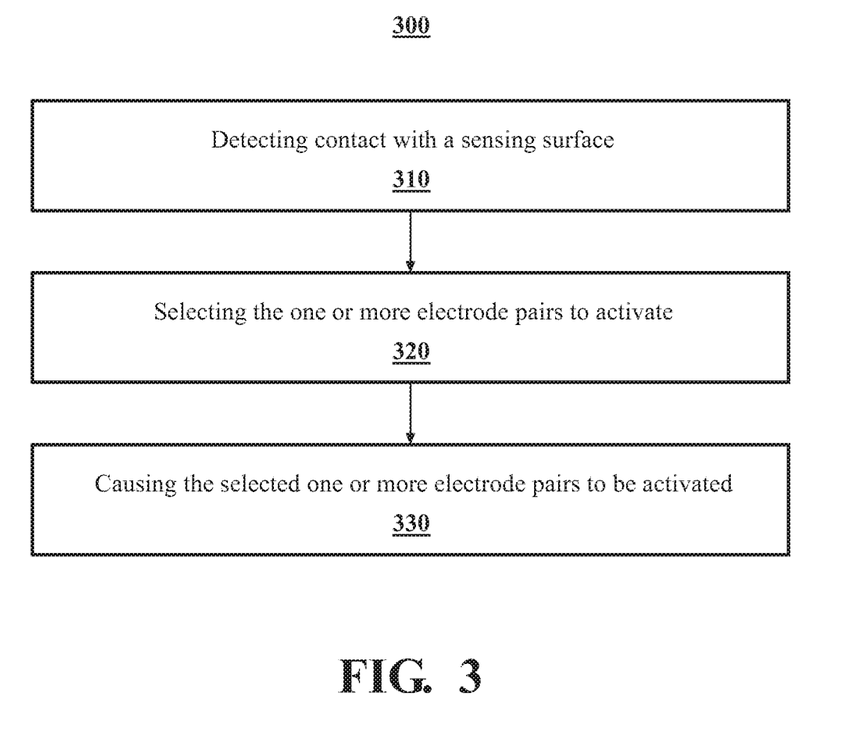
FIG. 3 is an example of a method for acquiring EDA.

Referring now to FIG. 3, an example of an EDA measuring method 300 is shown. The method 300 can be directed to actions being performed by one or more of the elements of the EDA acquisition system 100.

At block 310, contact with a sensing surface 102 can be detected. The contact can be detected by the one or more sensors 110. In some arrangements, it can be determined whether a user's finger or a user's palm is in contact with the sensing surface 102. The FPD module(s) 132 can determine whether the user's finger or the user's palm is in contact with the sensing surface 102. The method 300 can continue to block 320.

At block 320, in response to detecting contact with the sensing surface 102, one or more electrode pairs 104 can be selected to be activated. The selection of the one or more electrode pairs 104 to activate can be performed by the EPS module(s) 130. As an example and as previously mentioned, the EPS module(s) 130 can select the electrode pairs 104 to activate based on at least one of signal quality and historical data. The method 300 can continue to block 330.

At block 330, in response to selecting one or more electrode pairs 104 to activate, the selected one or more electrode pairs 104 can be activated. The EPA module(s) 134 can cause the electrode pairs 104 to be activated.

The method 300 can end. Alternatively, the method 300 can return to block 310 or to some other block. The method 300 can be repeated at any suitable point, such as at a suitable time or upon the occurrence of any suitable event or condition (e.g., a change in hand position or contact area).

The method 300 can include additional and/or alternative blocks to those described above. For instance, in some arrangements, the parasitic resistance for the activated electrode pairs 104 can be determined. In some arrangements, the EAE module(s) 138 can acquire EDA data from the user using the activated electrode pairs 104. In some arrangements, the EDA data can be evaluated and/or transmitted to any interested entity.

Figure 4A:
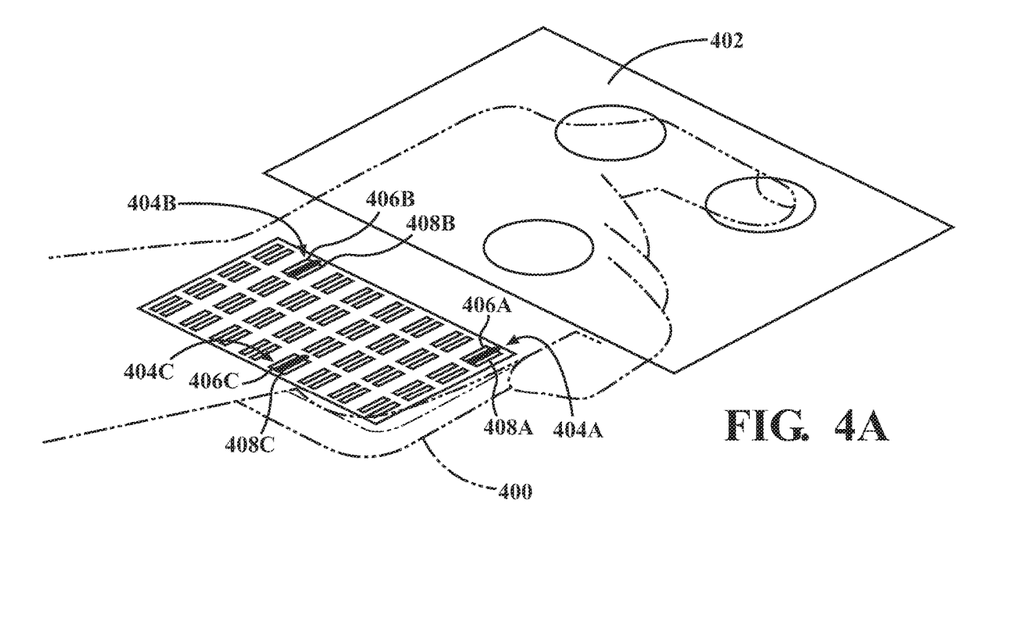
FIG. 4A-4B are examples of an EDA acquisition scenario.
Figure 4B:
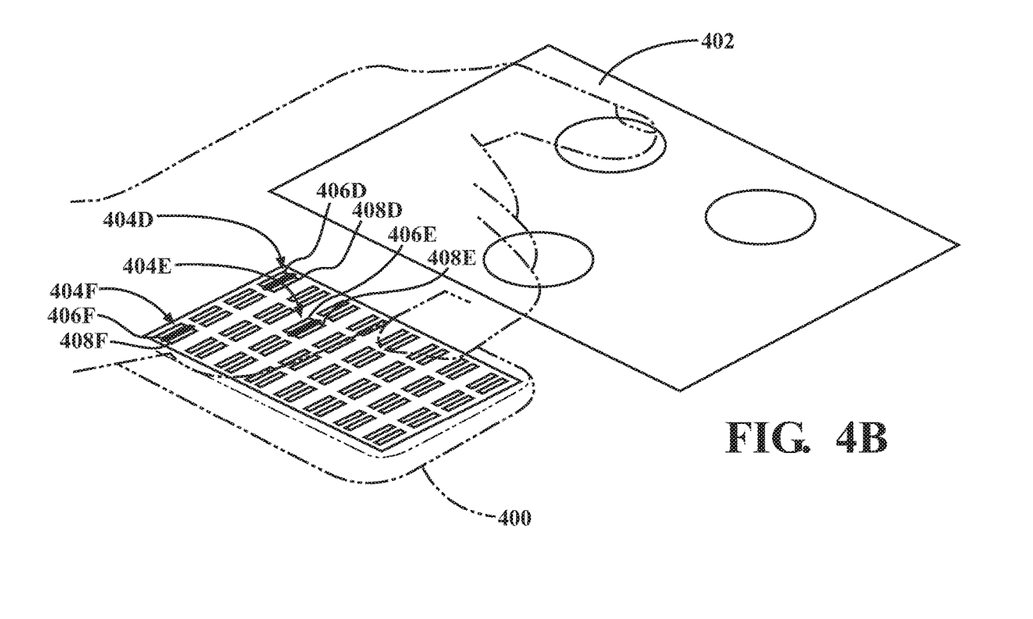

A non-limiting example of the operation of the EDA acquisition system 100 and/or one or more of the methods will now be described in relation to FIGS. 4A-4B. FIGS. 4A-4B show an example of an EDA acquisition and measuring scenario. Referring to FIGS. 4A-4B, a user can rest his or her palm on a handrest 400 while operating a vehicle user interface 402.

As shown in FIG. 4A, the user places his or her palm on top of the handrest 400, which includes the sensing surface 102. The sensors 110 can detect contact with the sensing surface 102. Based on the detected contact with the sensing surface 102, the FPD module(s) 132 can determine whether the user's finger(s) or palm is in contact with the sensing surface 102. In this case, the FPD module(s) 132 can receive information from the sensors 110 such as the force touch sensor(s) 114 indicating that a relatively even force is being applied to the sensing surface 102. The FPD module(s) 132 can determine that the surface area corresponding to the applied force on the sensing surface 102 is significantly wider than the width of a human finger, and as such can determine that the user's palm is in contact with the sensing surface 102.

The EPS module(s) 130 can select the electrode pairs 404 to activate based on current conditions such as signal quality. Alternatively or additionally, the EPS module(s) 130 can select the electrode pairs 404 based on historical data such as signal quality and the frequency of use of the electrode pairs 404 in contact with the user's palm. In this example, the EPS module(s) 130 can select three electrode pairs 404A, 404B, 404C. The EPA module(s) 134 can activate the selected electrode pairs 404A, 404B, 404C. Activating the electrode pairs 404A, 404B, 404C can causes the first electrodes 406A, 406B, 406C to have a negative polarity, the second electrodes 408A, 408B, 408C to have a positive polarity. A low voltage can travel through the skin of the user from the second electrode 408A, 408B, 408C to the first electrode 406A, 406B, 406C, respectively.

The parasitic resistance between the activated electrode pairs 404 can be determined based on the material of the sensing surface 102 and the distance between the activated electrode pairs 404A, 404B, 404C. The skin conductance sensor(s) 118 can measure the conductivity of the skin on the user's palm. The EAE module(s) 138 can determine the EDA data based on the conductivity measured by the skin conductance sensor(s) 118 and the parasitic resistance. Upon calculating the EDA data, the EAE module(s) 138 can transmit the resulting EDA data through the communication module(s) 140 to the user's mobile device and/or to one or more vehicle components and/or systems, such as the processor(s) 120.

As shown in FIG. 4B, the user has moved his or her hand from the position shown in FIG. 4A. The sensor(s) 110 can detect there is no longer contact between the previously selected electrode pairs 404 and the user's palm. The sensors 110 can also detect contact at another portion of the sensing surface 102. The EPA module(s) 134 can deactivate the previously selected electrode pairs 404A, 404B, 404C by, as an example, powering down the control switch(es) associated with the previously selected electrode pairs 404A, 404B, 404C. The EPS module(s) 130 can select one or more electrode pairs 404D, 404E, 404F to be activated based on the electrode pairs 404D, 404E, 404F in contact with the user's hand and historical data. The EPA module(s) 134 can activate the selected electrode pairs 404D, 404E, 404F. The selected electrode pair 404D includes a first electrode 406D and a second electrode 408D. The selected electrode pair 404E includes a first electrode 406E and a second electrode 408E. The selected electrode pair 404F includes a first electrode 406F and a second electrode 408F. The skin conductance sensor(s) 118 can measure the conductivity across the selected electrode pairs 404D, 404E, 404F. The parasitic resistance can be determined. The EDA data can be evaluated based on the parasitic resistance. The resulting EDA data can be transmitted, as mentioned in the example above, through the communication module(s) 140 to the user's mobile device and/or one or more vehicle components and/or systems, such as the processor(s) 120.

It will be appreciated that arrangements described herein can provide numerous benefits, including one or more of the benefits mentioned herein. For example, arrangements described herein facilitate acquiring and measuring the electrodermal activity of a user. Arrangements described herein can acquire the electrodermal activity of the user in a non-invasive manner. Arrangements described herein can acquire EDA measurements without a continuous connection to the user's skin. Arrangements described herein can acquire EDA measurements without the use of glued electrodes or electrodes hardly pressed against the skin. Arrangements described herein can provide accurate electrodermal activity measurements. Arrangements described herein can result in reduced computing and processing power requirements. Arrangements described herein can result in identifying the emotional state of a user.

The flowcharts and block diagrams in the figures illustrate the architecture, functionality, and operation of possible implementations of systems, methods and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or other apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein may take the form of a computer program product embodied in one or more computer-readable media having computer-readable program code embodied or embedded, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk drive (HDD), a solid state drive (SSD), a random access memory (RAM), a read-only memory (ROM), an erasable programmable read-only memory (EPROM or Flash memory), an optical fiber, a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object oriented programming language such as Java™ Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

As used herein, the term "substantially" or "about" includes exactly the term it modifies and slight variations therefrom. Thus, the term "substantially equal" means exactly equal and slight variations therefrom. "Slight variations therefrom" can include within 15 percent/units or less, within 14 percent/units or less, within 13 percent/units or less, within 12 percent/units or less, within 11 percent/units or less, within 10 percent/units or less, within 9 percent/units or less, within 8 percent/units or less, within 7 percent/units or less, within 6 percent/units or less, within 5 percent/units or less, within 4 percent/units or less, within 3 percent/units or less, within 2 percent/units or less, or within 1 percent/unit or less. In some instances, "substantially" can include being within normal manufacturing tolerances.

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e. open language). The phrase "at least one of . . . and . . . " as used herein refers to and encompasses any and all possible combinations of one or more of the associated listed items. As an example, the phrase "at least one of A, B and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope of the invention.

What is claimed is:

1. A method for measuring electrodermal activity (EDA), the method comprising:
   detecting, using one or more sensors, contact with a sensing surface, the sensing surface having a plurality of electrode pairs, each electrode pair including a first electrode and a second electrode, the first electrode and the second electrode being electrically isolated from each other, the plurality of electrode pairs being electrically isolated from each other, the plurality of electrode pairs being substantially parallel to each other, a distance between two directly adjacent electrode pairs being larger than a distance between the first electrode and a second electrode of each electrode pair, no intervening conductive structure is located between the two directly adjacent electrode pairs;
   responsive to detecting the contact with the sensing surface, selecting one or more electrode pairs to activate; and
   responsive to selecting one or more electrode pairs to activate, causing the selected one or more electrode pairs to be activated.

2. The method of claim 1, further comprising:
   acquiring EDA data from a user based on the contact with the sensing surface, using the one or more activated electrode pairs.

3. The method of claim 2, further comprising:
   when two or more electrode pairs are activated, determining parasitic resistance between the two or more activated electrode pairs; and
   evaluating the EDA data based on the determined parasitic resistance.

4. The method of claim 2, wherein acquiring EDA data from the user includes measuring EDA using at least one of: skin potential, resistance, conductance, admittance, and impedance.

5. The method of claim 1, further comprising:
   determining whether a user's finger or palm is in contact with the sensing surface.

6. The method of claim 5, further comprising:
   acquiring EDA data from a user, based on the contact with the sensing surface, using the one or more activated electrode pairs; and
   evaluating the EDA data based on the determination of whether the user's finger or palm is in contact with the sensing surface.

7. The method of claim 1, wherein selecting the one or more electrode pairs to activate includes:
   selecting the one or more electrode pairs to activate based on at least one of signal quality and historical data.

8. The method of claim 1, wherein the one or more sensors include at least one of a capacitive touch sensor, a force sensor and an optical sensor.

9. The method of claim 1, wherein the distance between the first electrode and the second electrode of the plurality of electrode pairs is substantially equal.

10. The method of claim 1, further comprising:
    detecting the contact with the sensing surface is broken;
    responsive to detecting the contact with the sensing surface is broken, causing one or more activated electrode pairs to deactivate;
    detecting another contact with the sensing surface;
    responsive to detecting the other contact with the sensing surface, selecting one or more electrode pairs to activate; and
    responsive to selecting the one or more electrode pairs to activate, causing the selected one or more electrode pairs to be activated.

11. A system for measuring electrodermal activity (EDA), the system comprising:
    a sensing surface, the sensing surface having a plurality of electrode pairs, each electrode pair including a first electrode and a second electrode, the first electrode and the second electrode being electrically isolated from each other, the plurality of electrode pairs being electrically isolated from each other, the plurality of electrode pairs being substantially parallel to each other, a distance between two directly adjacent electrode pairs being larger than a distance between the first electrode and a second electrode of each electrode pair, no intervening conductive structure is located between the two directly adjacent electrode pairs;

one or more sensors, the one or more sensors being configured to detect contact with the sensing surface; and one or more processors, the one or more processors being operatively connected to the plurality of electrode pairs, the one or more processors being operatively connected to the one or more sensors, the one or more processors being programmed to initiate executable operations comprising:

responsive to detecting contact with the sensing surface, selecting one or more electrode pairs to activate; and responsive to selecting one or more electrode pairs to activate, causing the selected one or more electrode pairs to be activated.

12. The system of claim 11, wherein the executable operations further include:

acquiring EDA data from a user based on the contact with the sensing surface, using the one or more activated electrode pairs.

13. The system of claim 12, wherein the executable operations further include:

when two or more electrode pairs are activated, determining parasitic resistance between the two or more activated electrode pairs; and evaluating the EDA data based on the determined parasitic resistance.

14. The system of claim 12, wherein acquiring EDA data from the user includes measuring EDA using at least one of: skin potential, resistance, conductance, admittance, and impedance.

15. The system of claim 11, wherein the executable operations further include:

determining whether a user's finger or palm is in contact with the sensing surface.

16. The system of claim 15, wherein the executable operations further include:

acquiring EDA data from a user, based on the contact with the sensing surface, using the one or more activated electrode pairs; and evaluating the EDA data based on the determination of whether the user's finger or palm is in contact with the sensing surface.

17. The system of claim 11, wherein selecting the one or more electrode pairs to activate includes:

selecting the one or more electrode pairs to activate based on at least one of signal quality and historical data.

18. The system of claim 11, wherein the one or more sensors include at least one of a capacitive touch sensor, a force sensor and an optical sensor.

19. The system of claim 11, wherein the sensing surface is at least one of a portion of a steering wheel and a user input pad.

20. The system of claim 11, wherein the distance between the first electrode and the second electrode of the plurality of electrode pairs is substantially equal.

* * * * *